(12) United States Patent
Ramsay et al.

(10) Patent No.: US 8,900,237 B2
(45) Date of Patent: Dec. 2, 2014

(54) MINIMALLY INVASIVE GUIDE SYSTEM

(75) Inventors: Christopher L. Ramsay, West Wareham, MA (US); Michael Mahoney, Middletown, RI (US); David Greg Anderson, Moorestown, NJ (US); Michael Wang, Miami, FL (US); Steven Ludwig, Baltimore, MD (US)

(73) Assignee: DePuy Synthes Products, LLC, Raynham, MA (US)

( * ) Notice: Subject to any disclaimer, the term of this patent is extended or adjusted under 35 U.S.C. 154(b) by 649 days.

(21) Appl. No.: 11/897,642

(22) Filed: Aug. 31, 2007

(65) Prior Publication Data

US 2009/0062857 A1    Mar. 5, 2009

(51) Int. Cl.
*A61B 17/90* (2006.01)
*A61B 17/17* (2006.01)
*A61B 17/70* (2006.01)

(52) U.S. Cl.
CPC ......... *A61B 17/1735* (2013.01); *A61B 17/1757* (2013.01); *A61B 17/7001* (2013.01); *A61B 17/7011* (2013.01); *Y10S 606/914* (2013.01)
USPC .......................... 606/86 A; 606/104; 606/914

(58) Field of Classification Search
USPC .......... 606/53, 60, 246, 250–279, 86 A, 86 B, 606/96–99, 104, 105, 105.5, 103; 403/76, 403/77
See application file for complete search history.

(56) References Cited

U.S. PATENT DOCUMENTS

| 4,653,481 | A |   | 3/1987  | Howland et al. |
|-----------|---|---|---------|----------------|
| 5,257,994 | A | * | 11/1993 | Lin ............................... 606/272 |
| 5,306,275 | A |   | 4/1994  | Bryan          |
| 5,474,551 | A |   | 12/1995 | Finn et al.    |

(Continued)

FOREIGN PATENT DOCUMENTS

| EP | 1339337 B1 | 9/2003 |
| EP | 1405606 A2 | 4/2004 |

(Continued)

OTHER PUBLICATIONS

Ebara, Sohei et al., "A New System for the Anterior Restoration and Fixation of Thoracic Spinal Deformities Using an Endoscopic Approach," *Spine*, vol. 25(7):876-883 (2000).

*Primary Examiner* — Jerry Cumberledge
(74) *Attorney, Agent, or Firm* — Nelson Mullins Riley & Scarborough LLP

(57) ABSTRACT

A minimally invasive fixation system and installation method is provided. The system includes a rod having an anchor fixation head, an anchor system for anchoring the rod using the anchor fixation head, and a guide system configured to attach to the anchor fixation head of the rod for the insertion of the additional anchor systems. In one embodiment, a method for placing a spinal fixation element relative to a vertebra is provided. The method includes inserting the spinal fixation element relative to the vertebra; connecting the spinal fixation element to a first vertebra with a first anchor; manipulating the spinal fixation element relative to the first anchor to align the spinal fixation element with a second vertebra; fixing the position of the spinal fixation element relative to the first bone anchor; determining an anchor site on a second vertebra using a guide system connected to the spinal fixation element; inserting a second anchor at an anchor site on second vertebra; and connecting the second anchor to the spinal fixation element to fix the spinal fixation element relative to the first vertebra and second vertebra.

9 Claims, 18 Drawing Sheets

(56) References Cited

U.S. PATENT DOCUMENTS

| | | | |
|---|---|---|---|
| 5,584,834 A | 12/1996 | Errico et al. | |
| 5,609,592 A | 3/1997 | Brumfield et al. | |
| 5,624,441 A | 4/1997 | Sherman et al. | |
| 5,984,922 A | 11/1999 | McKay | |
| 6,015,409 A * | 1/2000 | Jackson | 606/278 |
| 6,468,276 B1 | 10/2002 | McKay | |
| 6,520,990 B1 * | 2/2003 | Ray | 623/17.11 |
| 6,562,038 B1 | 5/2003 | Morrison | |
| 6,626,906 B1 | 9/2003 | Young | |
| 6,648,507 B2 | 11/2003 | Joshi et al. | |
| 6,726,692 B2 | 4/2004 | Bette et al. | |
| 6,770,075 B2 | 8/2004 | Howland | |
| 6,964,665 B2 | 11/2005 | Thomas et al. | |
| RE39,035 E | 3/2006 | Finn et al. | |
| 7,166,108 B2 | 1/2007 | Mazda et al. | |
| 7,179,261 B2 | 2/2007 | Sicvol et al. | |
| 7,527,638 B2 | 5/2009 | Anderson et al. | |
| 7,666,188 B2 | 2/2010 | Anderson et al. | |
| 7,794,464 B2 * | 9/2010 | Bridwell et al. | 606/86 A |
| 7,922,727 B2 * | 4/2011 | Songer et al. | 606/86 A |
| 8,025,682 B2 | 9/2011 | Mahoney et al. | |
| 8,057,518 B2 | 11/2011 | Frasier et al. | |
| 8,075,591 B2 | 12/2011 | Ludwig et al. | |
| 8,512,343 B2 | 8/2013 | Dziedzic et al. | |
| 2003/0187431 A1 | 10/2003 | Simonson | |
| 2004/0204710 A1 * | 10/2004 | Patel et al. | 606/53 |
| 2004/0236330 A1 | 11/2004 | Purcell et al. | |
| 2005/0085824 A1 * | 4/2005 | Castaneda | 606/98 |
| 2005/0245928 A1 * | 11/2005 | Colleran et al. | 606/61 |
| 2006/0030839 A1 * | 2/2006 | Park et al. | 606/1 |
| 2006/0089651 A1 | 4/2006 | Trudeau et al. | |
| 2006/0095037 A1 * | 5/2006 | Jones et al. | 606/61 |
| 2006/0095044 A1 * | 5/2006 | Grady et al. | 606/96 |
| 2006/0100637 A1 * | 5/2006 | Rathbun et al. | 606/96 |
| 2006/0111730 A1 | 5/2006 | Hay | |
| 2006/0116679 A1 * | 6/2006 | Lutz et al. | 606/69 |
| 2006/0122607 A1 * | 6/2006 | Kolb | 606/71 |
| 2006/0155278 A1 | 7/2006 | Warnick | |
| 2006/0167454 A1 * | 7/2006 | Ludwig et al. | 606/61 |
| 2006/0173456 A1 | 8/2006 | Hawkes et al. | |
| 2006/0200135 A1 * | 9/2006 | Sherman et al. | 606/61 |
| 2006/0217735 A1 * | 9/2006 | MacDonald et al. | 606/90 |
| 2006/0247630 A1 * | 11/2006 | Iott et al. | 606/61 |
| 2006/0264934 A1 * | 11/2006 | Fallin | 606/61 |
| 2006/0271050 A1 * | 11/2006 | Piza Vallespir | 606/61 |
| 2006/0282074 A1 | 12/2006 | Renaud et al. | |
| 2007/0093838 A1 * | 4/2007 | Khodadadyan-Klostermann et al. | 606/70 |
| 2007/0173831 A1 * | 7/2007 | Abdou | 606/61 |
| 2007/0213716 A1 * | 9/2007 | Lenke et al. | 606/61 |
| 2007/0270820 A1 * | 11/2007 | Dickinson et al. | 606/61 |
| 2008/0125788 A1 * | 5/2008 | Cohen et al. | 606/104 |
| 2009/0062822 A1 | 3/2009 | Frasier et al. | |
| 2009/0062864 A1 | 3/2009 | Ludwig et al. | |

FOREIGN PATENT DOCUMENTS

| | | |
|---|---|---|
| WO | WO-98/49961 A1 | 11/1998 |
| WO | WO-2004/080318 A1 | 9/2004 |
| WO | WO-2006/023514 A1 | 3/2006 |
| WO | WO-2006/047742 A2 | 5/2006 |
| WO | WO-2006/081375 A2 | 8/2006 |

* cited by examiner

MINIMALLY INVASIVE GUIDE SYSTEM

FIELD OF THE INVENTION

The present invention relates to a spinal connection device and method for use during orthopedic surgery. More particularly, the present invention relates to a system for coupling a rod to a vertebra for use with a rod-first surgical system.

BACKGROUND OF THE INVENTION

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive devices and methods for implanting spinal fixation devices. One such method, for example, utilizes two percutaneous access devices for implanting an anchoring device, such as a spinal screw, into adjacent vertebrae. A rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle.

Accordingly, there remains a need for improved methods and devices for introducing spinal fixation elements, anchor systems, and/or other spinal devices into a patient's spine.

SUMMARY OF THE INVENTION

In accordance with a first aspect, a minimally invasive rod-first fixation system is provided. The system includes a rod having an anchor fixation head, an anchor system for anchoring the rod using the anchor fixation head, and a guide system configured to attach to the anchor fixation head of the rod for the insertion of the additional anchor systems.

In certain embodiments, the anchor fixation head of the rod may be configured to engage a specific type of anchor system. The anchor fixation head of the rod may also have configuration for attaching the guide system to the rod.

In certain embodiments, the anchor may be an anchor screw system. In other embodiments the anchor system may be an anchor bolt system.

In certain embodiments, the guide system includes a guide portion, a rod-engaging member, and a plurality of targeting members. The guide portion adapted to be positioned outside a patient's body and to extend along a patient's spinal column. The rod-engaging member is mated to the guide portion and adapted to couple to the anchor fixation head of the rod and to maintain the rod in a fixed position within the patient's body extending adjacent to a patient's spinal column. The one or more targeting members are slidably coupled to the guide portion. Each targeting member is adapted to target an implant site on a vertebra in the patient's spinal column.

In accordance with another aspect, a method for placing a spinal fixation element relative to a vertebra is provided. The method comprises connecting the spinal fixation element to a first vertebra with a first anchor; manipulating the spinal fixation element relative to the first anchor to align the spinal fixation element with a second vertabra; fixing the position of the spinal fixation element relative to the first bone anchor; determining an anchor site on a second vertebra using a guide system connected to the spinal fixation element; inserting a second anchor at anchor site on second vertebra; and connecting the second anchor to the spinal fixation element to fix the spinal fixation element relative to the first vertebra and second vertebra.

In an exemplary embodiment, the rod may be inserted through a first incision, and each anchor may be inserted through an incision separate from the spinal fixation element and one another. Once the anchor(s) are implanted, the rod may be moved, e.g., approximated, toward the anchor (s) to couple, statically or dynamically, the rod to the anchor (s). In one exemplary method, the rod may be locked to the anchor (s) to maintain the vertebrae in a fixed position relative to one another.

Also disclosed herein are various techniques for determining an implant site on each vertebra. In one exemplary embodiment, a targeting member may be positioned relative to a target implant site on a vertebra, and the targeting member may be aligned relative to the target implant site using an imaging device. The targeting member may be part of a guide system having a guide portion that is adapted to be positioned outside a patient's body and to extend along a patient's spinal column, and a rod-engaging member that is adapted to couple to the spinal fixation element to maintain the rod in a fixed position within the patient's body extending adjacent to a patient's spinal column. The targeting members may be slidably disposed on the guide portion to allow each targeting member to be adjusted relative to a target implant site on a vertebra.

Various techniques for implanting the anchor system(s) are also disclosed herein. In one exemplary embodiment, one or more anchor systems can be percutaneously delivered to the anchor site through a cannula which may be positioned through a minimally invasive pathway to the anchor system site. Each cannula may be attached to a guide system that is adapted to couple to the rod.

BRIEF DESCRIPTION OF THE FIGURES

These and other features and advantages of the instruments and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Disclosed herein are system and method for spinal fixation. A person skilled in the art will appreciate that, while the methods are described in connection with certain spinal instruments and devices, a variety of spinal instruments and devices can be used to perform the methods in accordance with the various embodiments disclosed herein. Conversely, the instruments and devices disclosed herein can be used for a variety surgical procedures. Moreover, a person skilled in the art will appreciate that exemplary methods can be performed in any sequence using only some or all of the methods.

System

Figure 1:
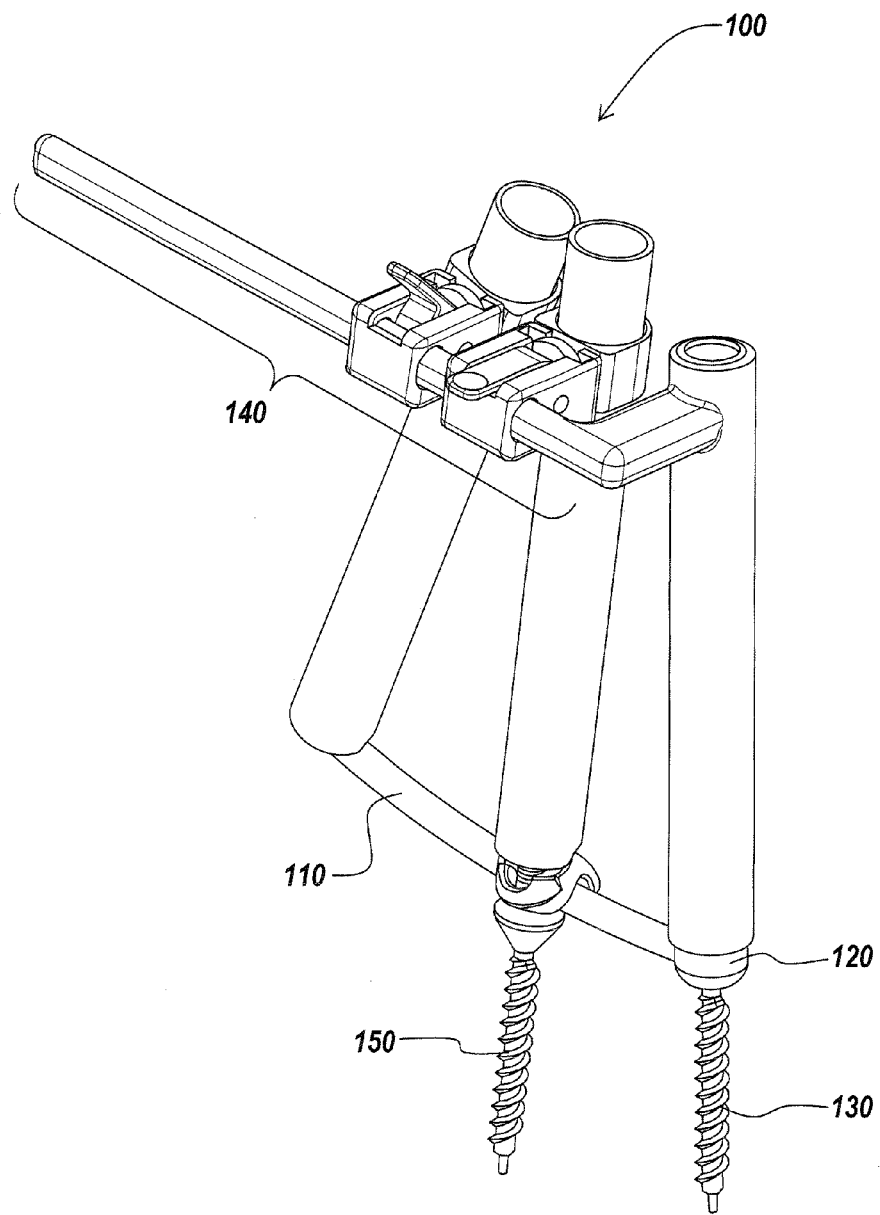
FIG. 1 illustrates an exemplary embodiment of a minimally invasive rod-first spinal fixation system of the present invention.

FIG. 1 illustrates an embodiment of a minimally invasive rod-first spinal fixation system 100 of the present invention. The system comprises a rod 110 having an anchor fixation head 120, a anchor system 130 for anchoring the rod 110 using the anchor fixation head 120; and a guide system 140 configured to attach to the anchor fixation head 120 of the rod 110 for the insertion of the additional anchor systems 150. Each element is configured to work in conjunction with the other elements. Each of these elements will be discussed below.

The rod 110 sized and dimensioned for use in minimally invasive surgical techniques. As such the rod may be sized and dimensioned to be inserted using a cannula or access port. In certain embodiments, the rod may also be channeled to assist in insertion using a guide wire. Further discussion of insertion techniques can be found below in the Spinal Fixation Element Introduction section.

As set forth above, the rod 110 of the system 100 includes an anchor fixation head 120. The anchor fixation head 120 provides an integrated fixation point for attaching the rod 110 to a vertebra to secure the position of the rod 110 relative to the spine of the patient. The anchor fixation head 120 also provides a location for attaching the guide system 140 to the rod 110.

The configuration of the anchor fixation head 120 may vary depending on the nature of the anchor fixation system(s) 130 and guide system 140 that are to be used in conjunction with the rod 110. Several examples of such configurations can be seen in FIG. 2.

Figure 2:
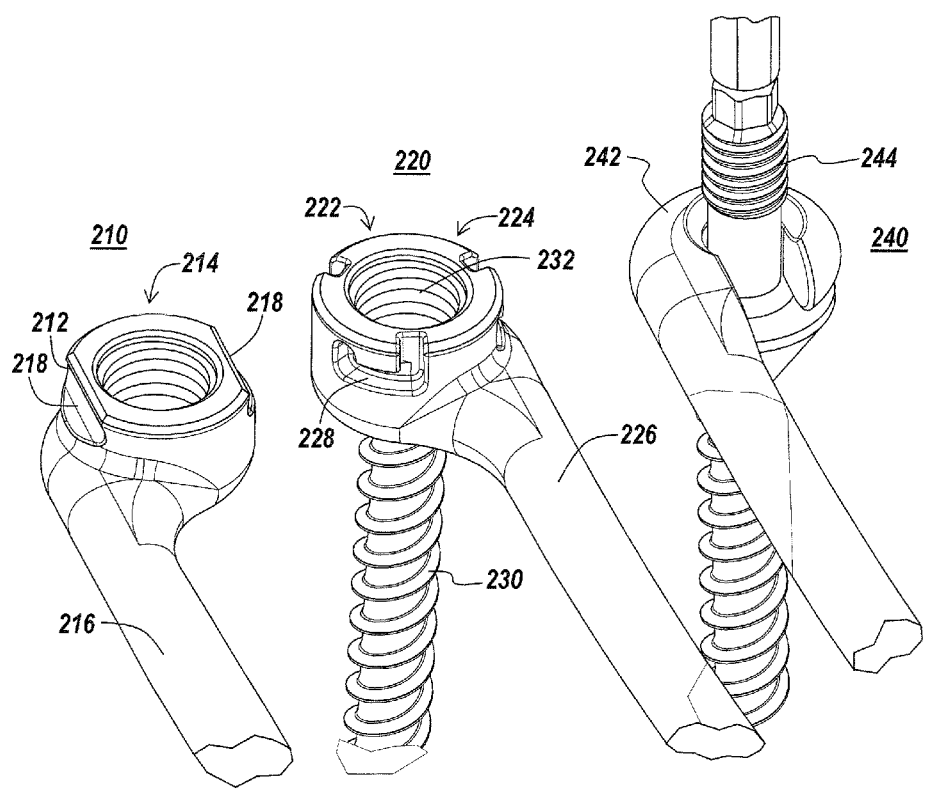
FIGS. 2A-2C illustrate various exemplary embodiments of the anchor fixation head of the rod of the system of the present invention.

FIG. 2 illustrates three different configurations 210, 220, and 240 of an anchor fixation head. In the first configuration 210, the anchor fixation head 212 forms an eyelet 214 for receiving an anchor screw system. The eyelet 214 is configured to mate with an anchor screw system to fix the location and position of the rod 216. The anchor screw system will be discussed in more detail below.

In the first configuration 210, the anchor fixation head 212 further includes surface configurations 218 for attaching a guide system. In this example the surface configurations 218 provide a snap-fit connection for the guide system. Other possible configurations may provide for threaded or twist-lock connections for the guide system.

In the second configuration 220, an anchor screw 230 of an anchor screw system is shown inserted into the eyelet 224 of the anchor fixation head 222. Once an anchor screw 230 is inserted, the eyelet 224 is configured allow the rod to pivot until a locking mechanism of the anchor screw system (not shown), such as a set-screw, is placed to fix the position of the rod 226. Internal threads 232 are provided in the eyelet 224 for engaging the set screw. The anchor screw system will be discussed in more detail below.

In the second configuration, the anchor fixation head 222 also includes surface configurations 228 for attaching a guide system. In this example the surface configurations 228 provide a locking mechanism. To engage the locking mechanism the guide system is placed onto the fixation head 220 and rotated to engage the lock.

While the previous two configurations 210 and 220 deal with anchor fixation heads designed to work in conjunction with a specifically designed anchor screw system, the anchor fixation head may also be designed to be used with more conventional anchoring means. In the third configuration 240, the anchor fixation head 242 is configured to interact with an anchor bolt. In this configuration 240 the anchor fixation head 242 is "C" shaped to be able to engage an anchor bolt 244. The anchor fixation head may be placed onto the anchor bolt 244 using the opening in the "C" shape and then secured by placing a locking mechanism, such as a nut (not shown) onto the bolt 244.

It should be apparent that the configurations 210, 220, and 240 of FIG. 2 are but a few of the possible configuration for the anchor fixation head of the rod. Other possible configurations, including various means for attaching a guide system, will be apparent to one skilled in the art given the benefit of this disclosure.

As discussed above, the anchor fixation head can be adapted to work with any number of rod anchoring systems but additional advantages can be achieved when the anchor fixation head is configured to be used in conjunction with a corresponding anchor screw system.

Figure 3:
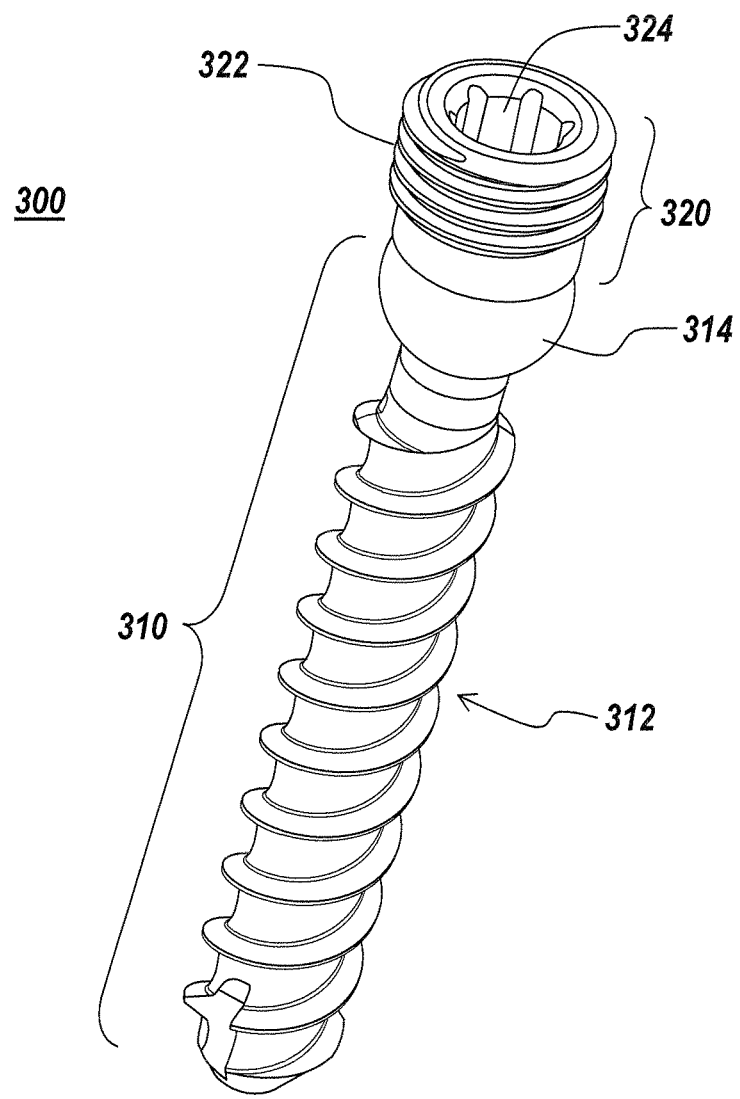
FIG. 3 illustrates an exemplary embodiment of a anchor screw system of the present invention.

FIG. 3 illustrates one embodiment of a anchor screw system 300. In this example the anchor screw system 300 includes an anchor screw 310 and a set screw 320. The anchor screw 310 is configured to mate with the anchor fixation head of the rod, as seen in FIG. 2, for attaching the rod to a vertebral body. The set screw 320 is configured to mate with the anchor fixation head for fixing the position of the rod on the anchor screw 310.

The screw 310 includes a shank portion 312 and head portion 314. The shank portion is threaded 316 for insertion into a vertebral body. The head portion 314 is configured to allow pivoting of the rod after the screw 310 has been inserted to attach the rod to a vertebra. In this example the head portion 314 is spherical in shape. The spherical head when combined with a corresponding anchor fixation head allows the rod to continue to rotate and pivot around the screw head portion 314. Once the rod is in the desired position, the position may be fixed by inserting a set screw 320.

The set screw is configured to fix the position of the rod on the head portion 314 of the screw. In the example of FIG. 3, the set screw 320 has threads 322 on the outer surface of the set screw to engage corresponding threads in the anchor fixation head (232 in FIG. 2). As the set screw 320 is tightened, the force exerted by the set screw 320 on the head portion 314 fixes the position of the rod. In certain embodiments the set screw 320 may further include a pass-thru 324 allowing for further adjustment to the screw 310 after placement of the set screw 320.

Preferably the anchor screw system is sized and dimensioned for use in minimally invasive surgical techniques. As such the rod may be sized and dimensioned to be inserted using a cannula or access port. It should also be apparent that the configuration 300 of FIG. 3 is but one possible configuration for the anchor fixation head of the rod. Other possible configurations will be apparent to one skilled in the art given the benefit of this disclosure.

Figure 4:
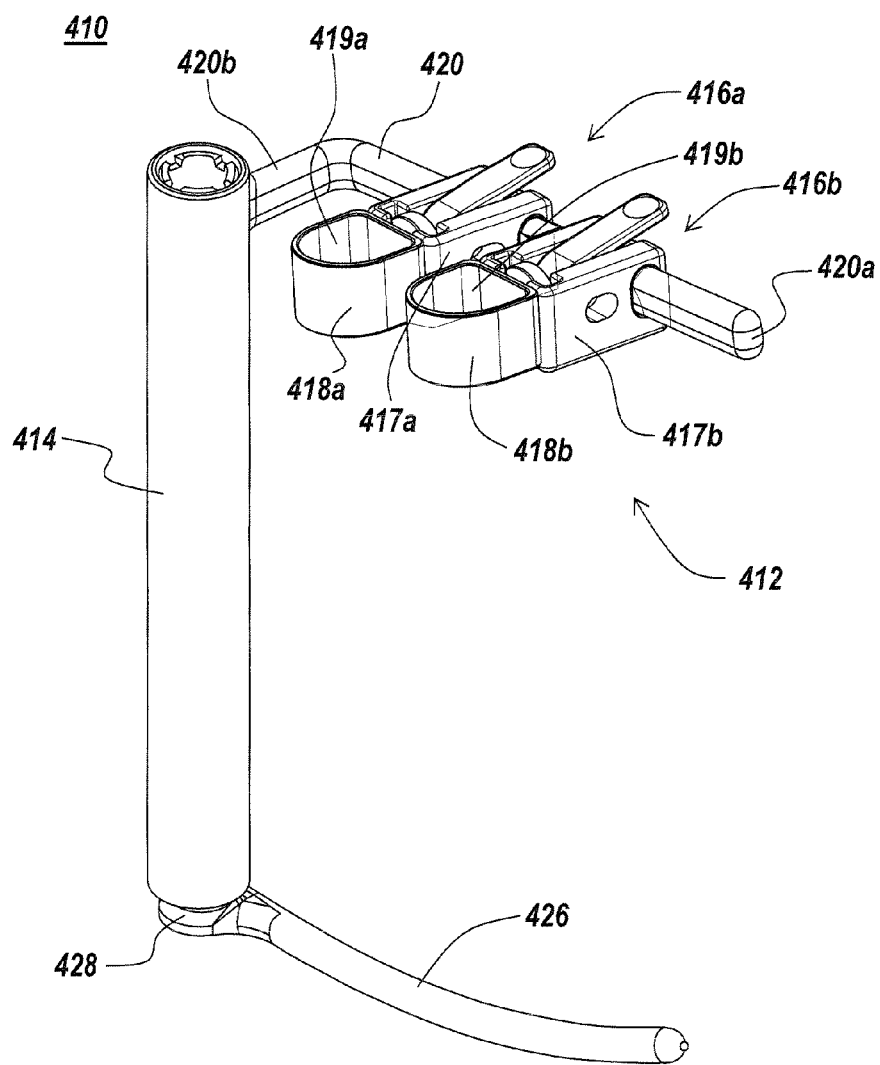
FIG. 4 illustrates an exemplary embodiment of a guide system of the present invention.

FIG. 4 illustrates an exemplary embodiment of a guide system 410 (guide system 140 in FIG. 1) that can be used to position a spinal fixation element, such as a rod, in a patient's spinal column, to target implant sites on one or more vertebra, and, in certain exemplary embodiments, to facilitate implanting an anchor in a vertebra. As shown, the guide system 410 generally includes a guide portion 412 that is adapted to be positioned outside a patient's body and a rod-engaging portion 414 that is adapted to couple to a rod 426 or other type of spinal fixation element, to maintain the rod 426 in a fixed position within the patient's body such that the rod 426 extends adjacent to a patient's spinal column. The rod-engaging portion 414 may be effective to maintain the rod 426 in a position that is substantially parallel to, but spaced apart from, the guide portion 412 such that guide portion 412 serves as a guide located outside of the body to indicate the location of the rod 426 disposed inside the patient's body. The guide system 410 can also include one or more targeting instruments 416a, 416b that are movably coupled to the guide portion 412 of the system 410. The targeting instruments 416a, 416b can be adapted to target an implant site on a vertebra in the patient's spinal column.

The guide portion 412 of the guide system 410 can have a variety of configurations. In one embodiment, for example, the guide system 410 is effective to indicate the position of a rod 426 disposed within and extending along a patient's spinal column. As shown in FIG. 4, the guide portion 412 has a generally elongate support rod 420 with opposed first and second ends 420a, 420b. The second end 420b may be adapted to couple to the rod-engaging portion 414. In the illustrated embodiment, the elongated support rod 420 is offset from the rod engaging portion 414 and rod 426 so that targeting instruments 416a, 416b target an implant site in-line with the rod 426.

The rod-engaging portion 414 can have virtually any shape and size. For example, in the illustrated embodiment, the rod engaging portion 414 is a cannula that extends in a direction that is transverse to the support rod 420 and it is adapted to removably engage an anchor fixation head 428 of the rod 426. The first end 414a of the rod-engaging portion 414 may be mated to the second end 420b of the support rod 420, and the second end 414b of the rod-engaging portion 414 is in engagement with a rod 426. While not illustrated, virtually any technique can be used to removably engage a rod 426 or other spinal fixation elements, including, for example, a clamping mechanism, a threaded engagement, an interference fit, twist-lock, etc. Some exemplary techniques for engaging a anchor fixation head 428 of the rod 426 have been previously discussed with respect to FIG. 2. The rod-engaging portion 414 can also include a locking mechanism (not shown) for locking the rod 426 relative to the rod-engaging portion 414, and for subsequently releasing the rod 426 from the rod-engaging portion 414.

The guide system 410 can also include one or more targeting instruments coupled thereto. As shown in FIG. 4, two targeting instruments 416a, 416b are slidably disposed on the support rod 420 of the guide portion 412. While a variety of targeting instruments and techniques can be employed, in an exemplary embodiment, as shown, one or more of the targeting instruments 416a, 416b may include a slidable support 417a, 417b and a targeting member 418a, 418b coupled to a terminal end of the support 417a, 417b. In certain exemplary embodiments, the targeting members 418a, 418b may be movably coupled to the supports 417a, 417b such that the targeting members 418a, 418b can be moved toward and away from the supports 417a, 417b, as well as angularly adjusted relative to the supports 417a, 417b. Such a configuration allows the targeting instrument 418a, 418b to be properly aligned with a target implant site on a vertebra. While one embodiment for targeting members 418a, 418b can be angularly adjustable, one skilled in the art will appreciate that the members can also be mounted at a fixed angle. Although not illustrated, guide portion 412 can initially be attached to rod-engaging portion 414 such that it extends in a direction opposite to that shown in FIG. 4 during rod insertion. This configuration can provide enhanced visibility and maneuverability during rod insertion.

While the targeting members 418a, 418b, can have a variety of configurations, U.S. Publication No. 2003/0187431 of Simonson entitled "Apparatus and Method for Targeting for Surgical Procedures," which is incorporated by reference herein in its entirety, discloses one such device for targeting an implant site. A person skilled in the art will appreciate that a variety of techniques and devices for targeting an implant site can be used with the present invention.

The targeting instruments 416a, 416b, can also be configured to facilitate use of the guide system 410, with other spinal tools and devices. For example, the targeting members 418a, 418b, can include an inner lumen 419a, 419b extending therethrough for receiving spinal tools and devices, such a drill guides, cannulae, and access ports. Alternatively, or in addition, the targeting members 418a, 418b, can be removably mated to the slidable support 417a, 417b, to allow each support member 417a, 417b, to mate to a cannula, access port, or other device or tool after the targeting members 418a, 418b, are removed. Each support 417a, 417b, can thus be used to maintain a cannula, access port, or other device in a fixed positioned relative to a target implant site, thereby providing a guided pathway to a target implant site on a vertebra, as will be discussed in more detail below.

Figure 5:
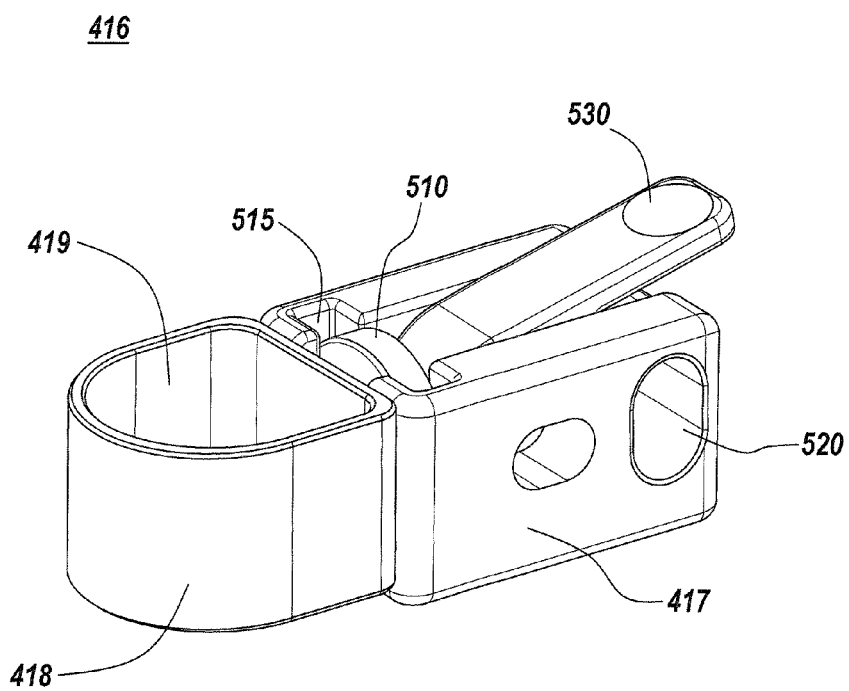
FIG. 5 illustrates an exemplary embodiment of a targeting instrument of a guide system of FIG. 4.

FIG. 5 illustrates detail of the targeting instrument 416. The targeting member 418 includes an inner lumen 419 extending therethrough for receiving spinal tools and devices, such a drill guides, cannulae, and access ports. The targeting member 418 also includes mating feature 510 configured to engage mating features 515 on the support member 417 for connecting the targeting member 418 to the support member 417. Mating features 510, 515, of the targeting member 418 and support member 417 allow for the removal of the targeting member 418. In this example, the mating features 510, 515 also allow the targeting member 418 to rotate in relation to the support member. This assists in targeting an implant site.

The support member 417 is configured to slide along a support rod 420 allowing for positioning of the targeting instrument 416. In this embodiment, the support member 417 has a channel 520 for receiving the support rod 420 of the guide system 410. In FIG. 5, the support member targeting instrument 416 further includes a locking mechanism, such as a cam mechanism 530 to secure the targeting member 418 to the support member 417 in a desired position. In certain embodiments, the cam mechanism 530 may further lock the position of the support member 417 on the support arm 420.

As discussed previously, the inner lumen 419 of the targeting member 418 is configured to receive a spinal tools and devices such as targets, cannulae, and access ports. Some examples of these can be seen in FIGS. 6 and 7.

Figure 6:
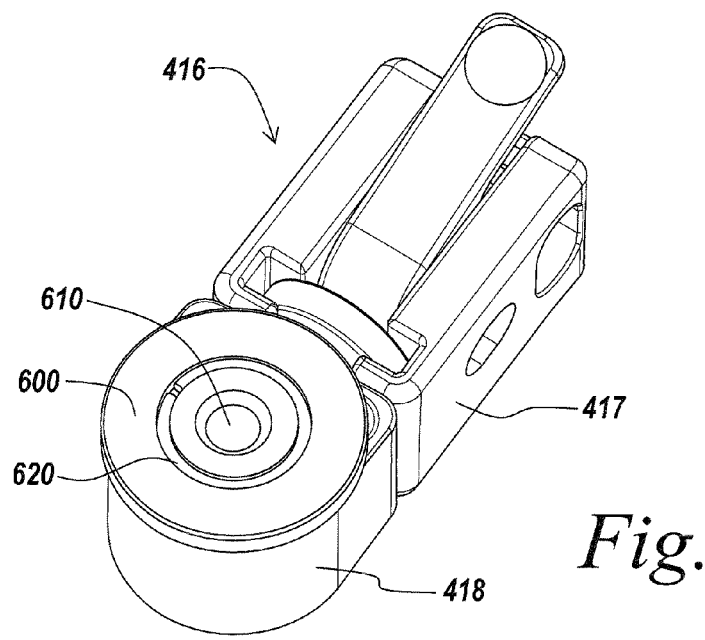
FIG. 6 illustrates an exemplary embodiment of a targeting insert for the target instrument of a guide system of the present invention.

FIG. 6 illustrates one embodiment of a targeting insert 600 that may be used in conjunction with a targeting instrument 416. Here the targeting insert is configured to be inserted into the inner lumen 419 of the targeting member 418. The targeting insert provides a lumen 610 of a smaller diameter than lumen 419 for guiding an instrument to an implant site. For example, the target insert 600 may be used to guide a guidewire to an implant site. In certain embodiments, the targeting insert may further include one or more radiographic markers 620 of different diameters to further assist in targeting.

Figure 7:
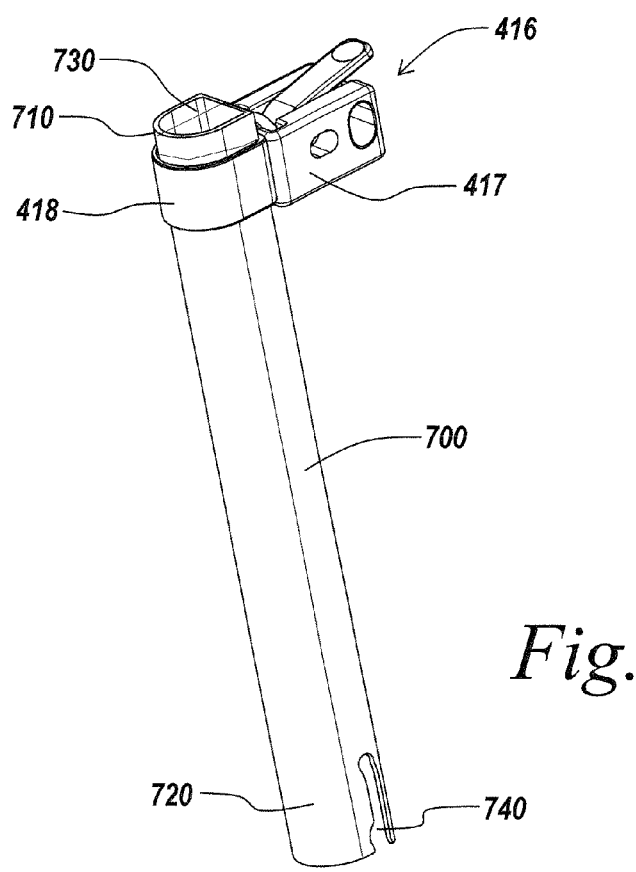
FIG. 7 illustrates an exemplary embodiment of a cannula for use with a guide system of the present invention.
Figure 8:
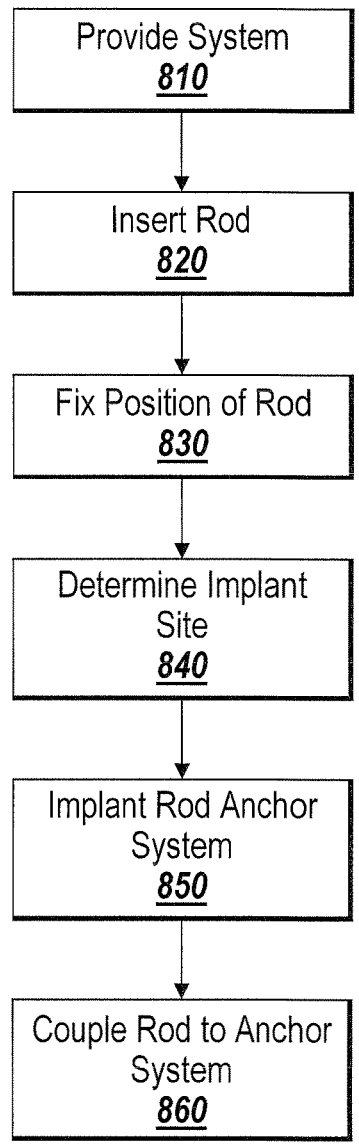
FIG. 8 is a flow chart of one exemplary method of the present invention.

FIG. 7 illustrates one embodiment of a cannula 700 that is mated with the targeting instrument 416. The cannula has a proximal end 710, a distal end 720, and a lumen 730 connecting the two ends 710, 720. In this example, the cannula 700 is configured to be held in position by the inner lumen 419 of the targeting member 418. In certain embodiments, the cannula may further include configurations 740 on the distal end for engaging a rod, the bone at an implant site, or any combination thereof. As previously noted, also disclosed herein are methods for providing minimally invasive spinal fixation. FIG. 8 illustrates a flow chart 800 of an exemplary embodiment of a method. In general, an exemplary method uses the fixation system discussed in FIG. 1 including a rod having an anchor fixation head; a anchor system for anchoring the rod using the rod head; and a guide system configured to attach to the anchor fixation head of the rod for the insertion of additional anchor systems. Of course, any number of spinal fixation elements (SFEs) my be placed using these methodology describe herein. The method involves inserting the spinal fixation element (SFE) relative to a vertebrae (step 810), connecting the spinal fixation element (SFE) to a first vertebra with a first anchor (step 820), manipulating the spinal fixation element (SFE) relative to the first anchor to align the spinal fixation element (SFE) with a second vertebra (step 830), fixing the position of the spinal fixation element (SFE) relative to the first bone anchor (step 840), determining an anchor site on the second vertebra using a guide system connected to the spinal fixation element (SFE) (step 850), inserting a second anchor at the anchor site on the second vertebra (step 860), and connecting the second anchor to the spinal fixation device to fix the spinal fixation element (SFE) relative to the first vertebra and second vertebra (step 870). Various exemplary techniques for performing the aforementioned various steps are discussed below under the following headings: Spinal Fixation Element Introduction, Position Fixation, Targeting, and Implanting Additional Anchor Systems.

Spinal Fixation Element Introduction

A variety of techniques can be used to insert a spinal fixation element, such as a rod, to extend along a patient's spinal column adjacent to two or more vertebra, and the spinal fixation element can be introduced at various locations along the patient's spine. For example, the spinal fixation element can be introduced through the same incision used to introduce a anchor system, or alternatively the spinal fixation element can be introduced through an incision that is separate from and located a distance apart from the incision(s) used to implant the anchor system(s). The spinal fixation element can also either be directly introduced through the incision to extend up along the patient's spinal column, or it can be introduced through a cannula, access port, or other device for guiding the spinal fixation element to extend along the patient's spinal column. Various tools can also be coupled to the spinal fixation element to manipulate and facilitate introduction and positioning of the spinal fixation element in the patient's body.

Figure 9A:
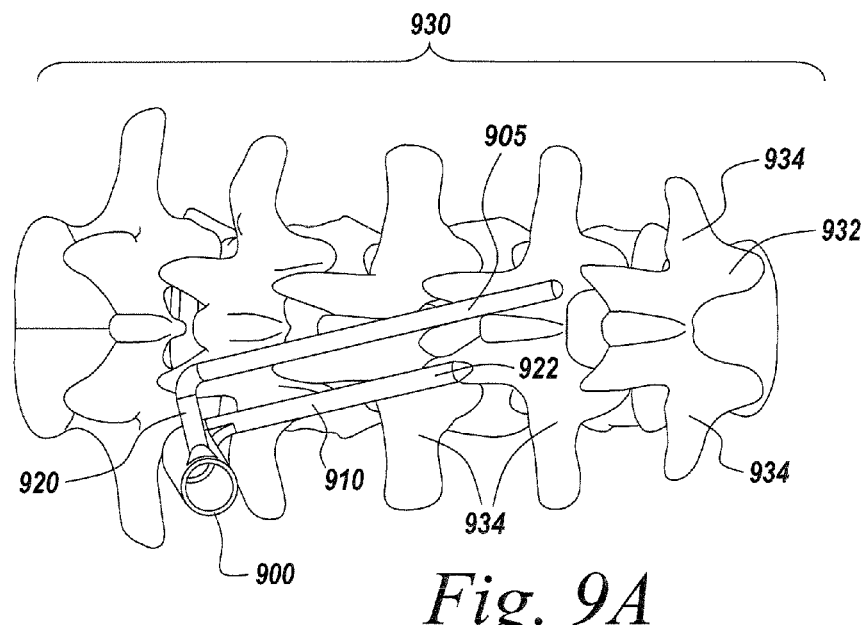
FIGS. 9A-E depict the process of inserting and positioning a rod along a patients spine.

In the example of FIGS. 9A-E, a rod 910 is attached to a guide system 900 using an anchor fixation head 920. In FIG. 9A the guide system 900 is manipulated to insert the rod 910 through an incision and to bluntly advance the rod 910 through the soft tissue. In certain embodiments, as seen in FIGS. 9A-E, the end of the rod 922 opposite the anchor fixation head 920 is configured to aid in the insertion of the rod 910.

Figure 9B:
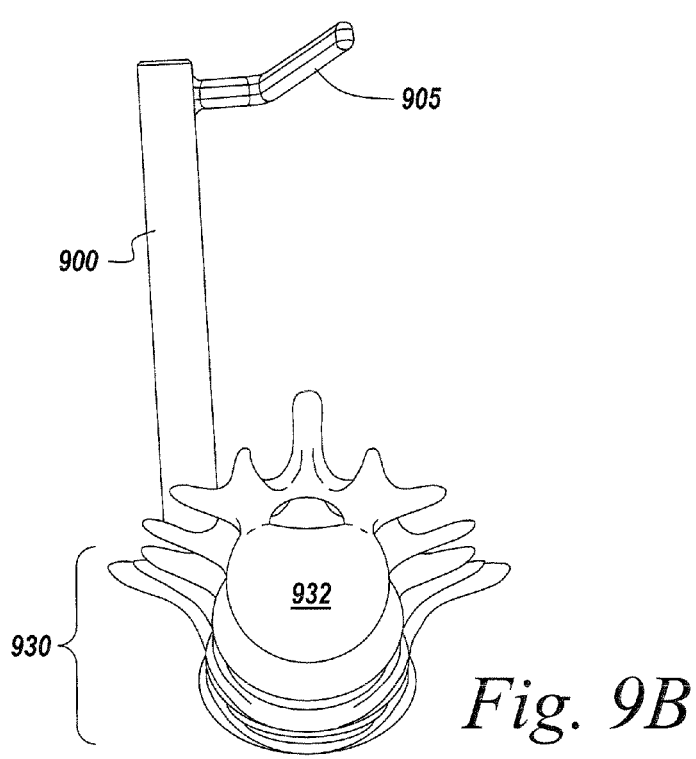
Figure 9C:
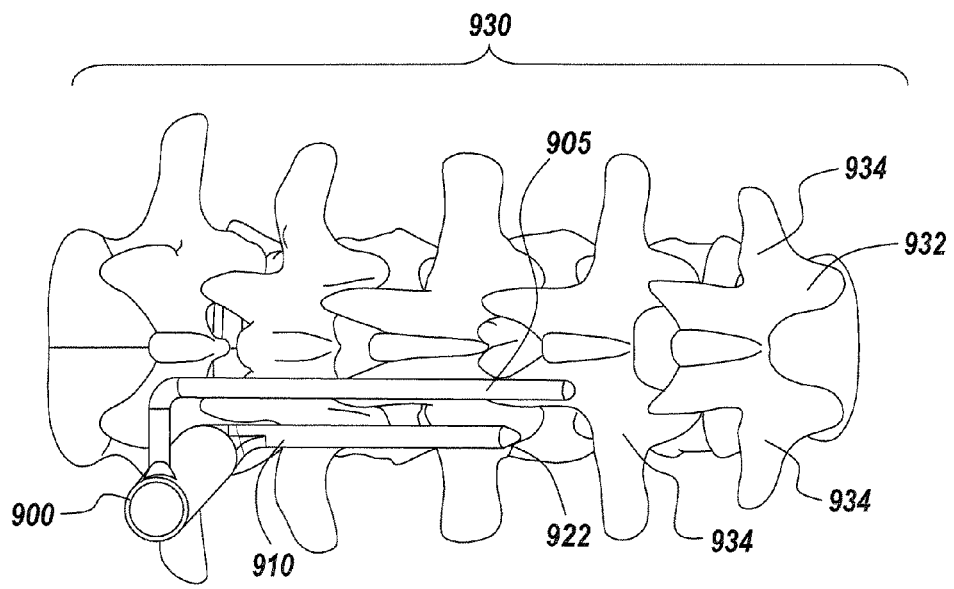
Figure 9D:
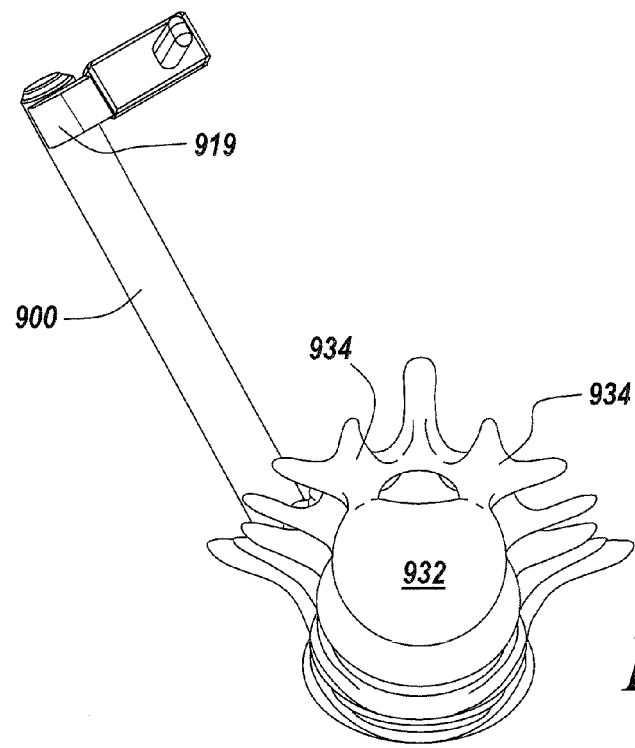
Figure 9E:
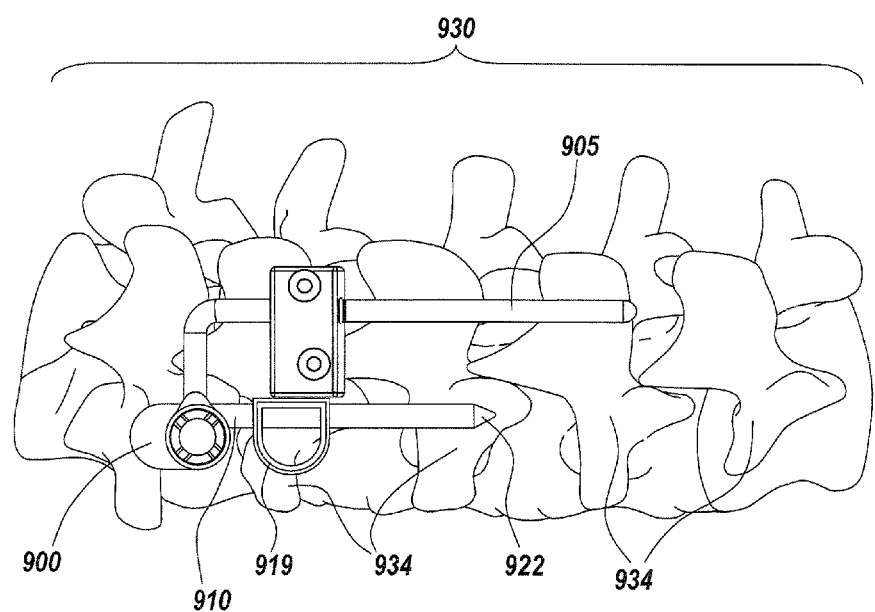

The guide system 900 and rod 910 may be inserted in any number of orientations that make insertion easier. For example, the rod may be inserted off axis with the patients spine 930, as seen in FIG. 9A, with the guide system 900 is in a vertical orientation, as seen in FIG. 9B, in order to get rod 910 inserted. Once inserted, the rod 910 may be manipulated or wanded into alignment with the pedicles 934 of the vertebra 932 using the external guide system 900 attached to the rod 910. An example of this can be seen in FIG. 9C. The proper position of the rod 910 can be determined using fluoroscopy.

Once the rod 910 is aligned with the pedicles 932, the guide system 910 and rod 900 may be further manipulated or wanded to align with the trajectory of the pedicles 934 for anchor insertion. An example of this can be seen in FIG. 9D. Again, the proper position of the rod 910 and guide 900 can be determined using fluoroscopy.

Once properly positioned, the position of the guide system 900, and the attached rod 910, is preferably fixedly attached to a support, such as the operating table, using, for example, a retractor arm. A top down view of such proper positioning can be seen in FIG. 9E. In this example, a targeting member 919 has been attached to the support arm In certain embodiments the rod may be inserted using a guide wire. In some such embodiments, the rod may be channeled to engage and work in conjunction with the guide wire for inserting the rod. The techniques for insertion of rod using a guide wire are similar to those for inserting a anchor system as discussed below.

Figure 10A:
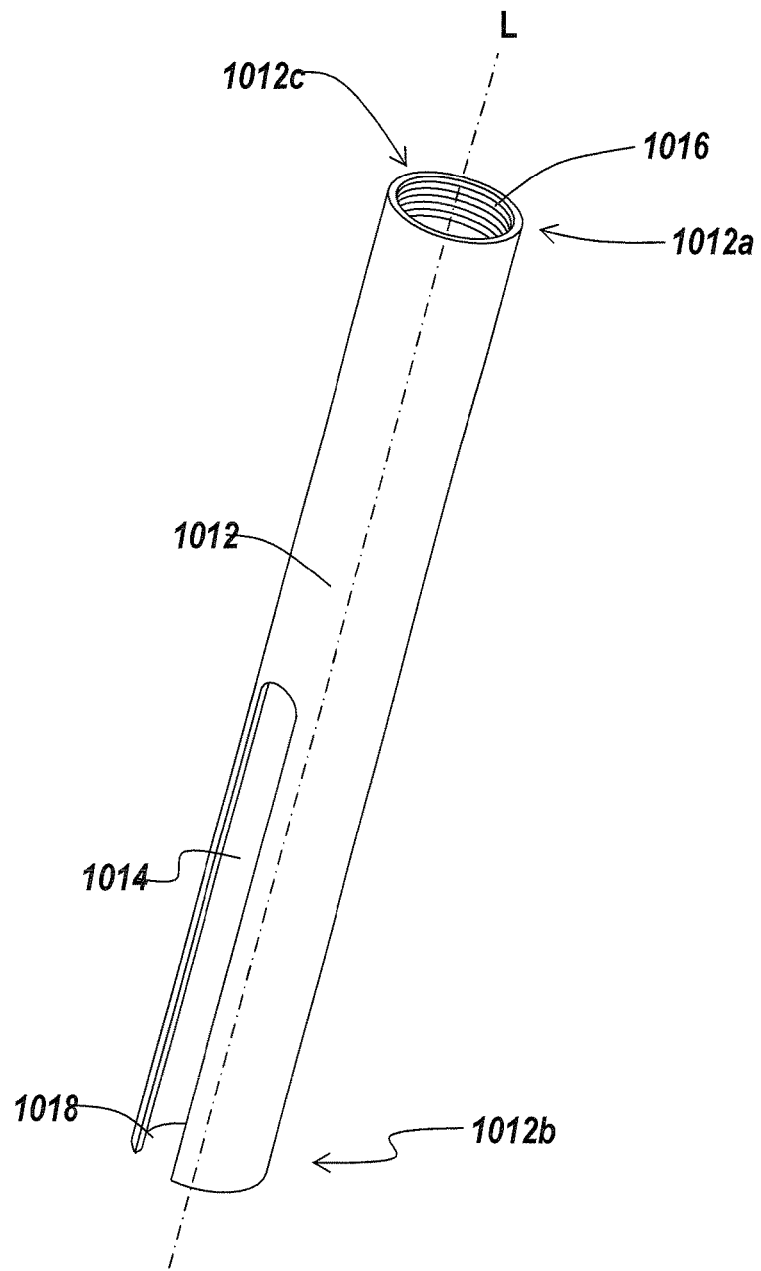
FIG. 10A is a side perspective view of an exemplary embodiment of a cannula for inserting the rod of the present invention.

In another exemplary embodiment, the rod can be introduced through a cannula. FIG. 10A illustrates an exemplary embodiment of a cannula 1012 for introducing a rod. As shown, the cannula 1012 is in the form of a generally elongate, cylindrical tube having an inner lumen 1012c formed therein and defining a longitudinal axis L that extends between proximal and distal ends 1012a, 1012b thereof. The cannula 1012 has a length that allows the proximal end 1012a of the cannula 1012 to be positioned outside the patient's body, while the distal end 1012b of the cannula 1012 extends into the patient's body to define a pathway for the rod. The cannula 1012 also includes at least one sidewall opening or slot 1014, and more preferably two opposed sidewall openings (only one opening 1014 is shown), formed therein and extending proximally from the distal end 1012b thereof. The openings 1014 allow the rod to be rotated from a position coaxial with the cannula 1012 to a position in which the rod extends along the spinal column.

Figure 10B:
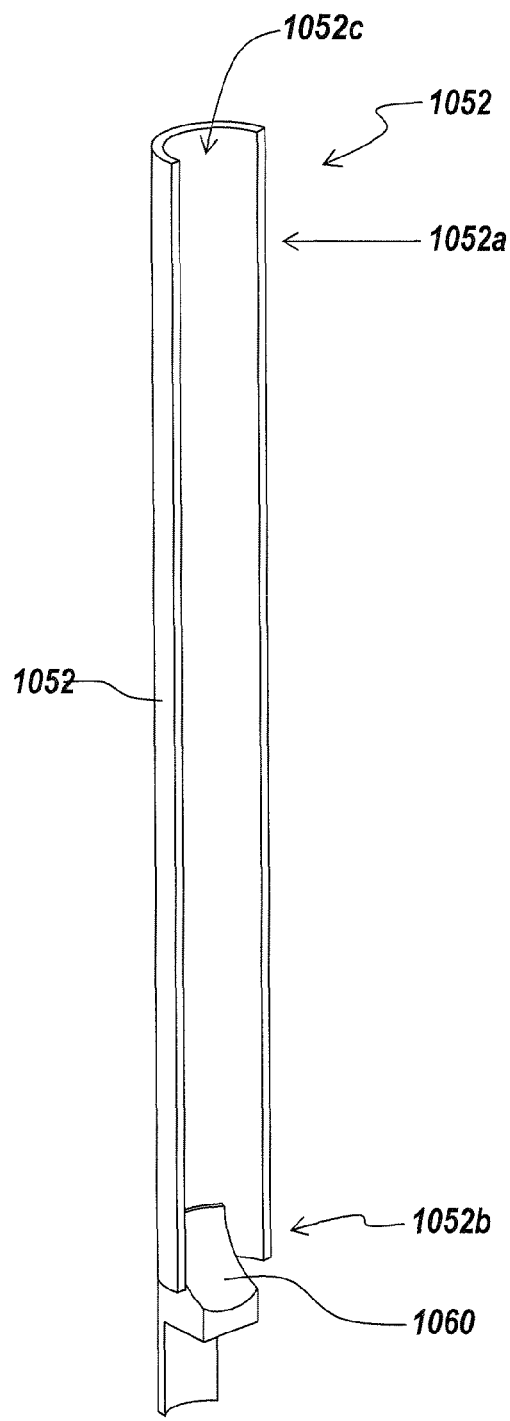
FIG. 10B is a cross-sectional, perspective view of another exemplary embodiment of a guide cannula for inserting the rod of the present invention.

In another embodiment, shown in FIG. 10B, an exemplary cannula 1052 can include a guide member 1060 formed within the distal end 1052b of the lumen 1052c to help guide the rod from the first orientation to the second orientation. The guide member 1060 is in the form of a sloped shelf formed within the inner lumen 1052c of the cannula 1052 and it is positioned opposite to a sidewall slot 1054 formed in the access device 1052. In use, as the leading end of a rod contacts the shelf 1060 and the shelf 1060 begins to direct the rod into the second orientation, thereby causing the rod to extend in a direction that is substantially transverse to the axis L of the device 1052, and that is preferably substantially parallel to the patient's spinal column.

Other exemplary techniques for introducing a rod through a cannula or access device and into a patient's body are described in more detail in U.S. patent application Ser. No. 10/738,130 of Anderson et al. entitled "Methods And Devices For Minimally Invasive Spinal Fixation Element Placement," and U.S. patent application Ser. No. 10/737,537 of Anderson et al. entitled "Methods And Devices For Spinal Fixation Element Placement." These references are incorporated by reference herein in their entirety.

Figure 11A:
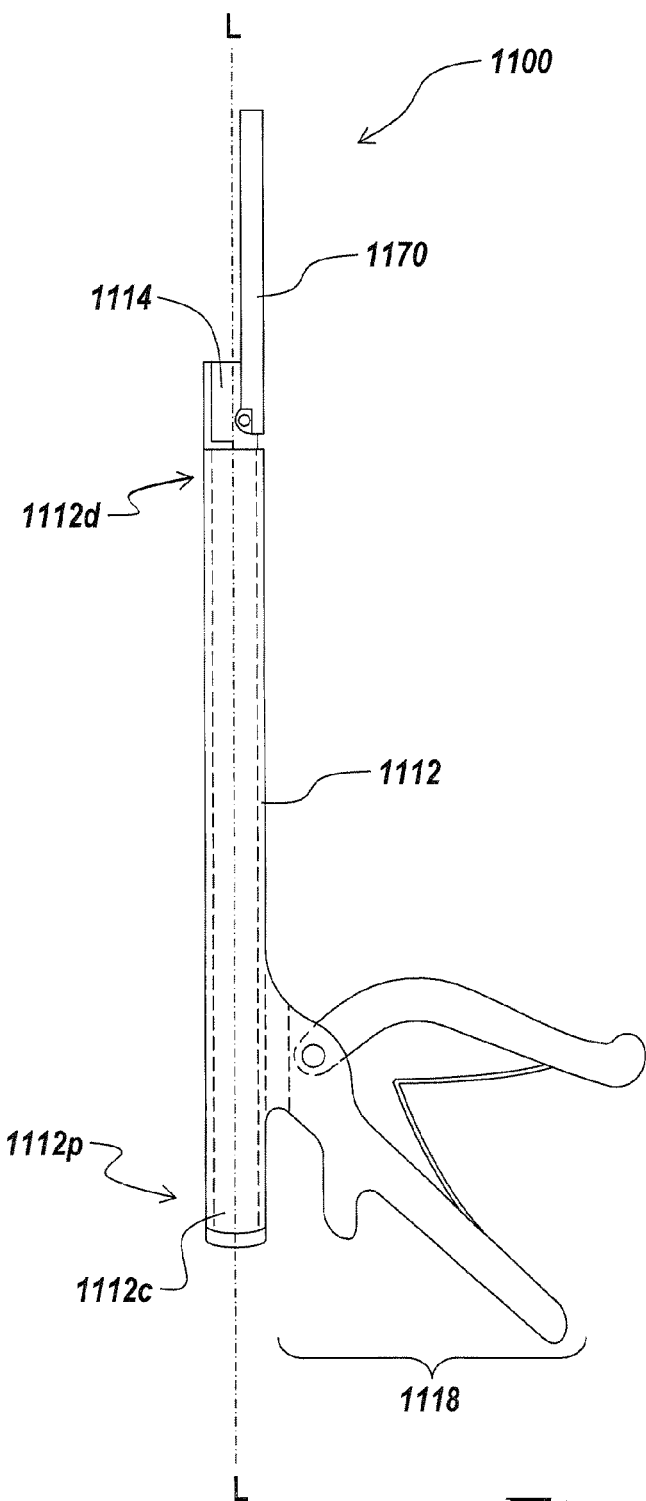
FIG. 11A is a side view of an exemplary pivoting implant holder having a spinal fixation element mated thereto and positioned in a first orientation adapted for introduction into a patient's spinal column.
Figure 11B:
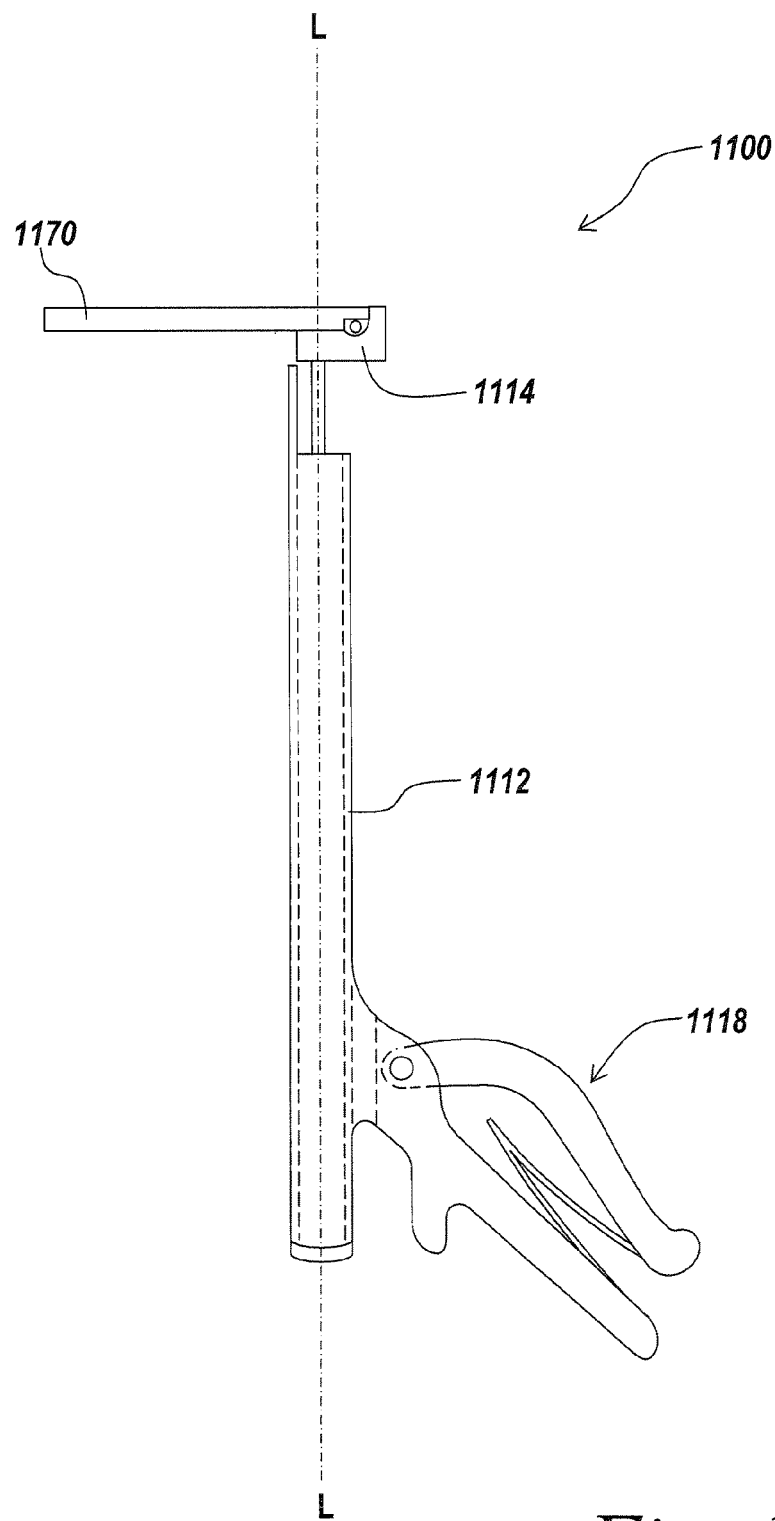
FIG. 11B is a side view of the pivoting implant holder shown in FIG. 11A with a spinal fixation element pivoted into a second orientation.

FIGS. 11A and 11B illustrate another exemplary embodiment of a technique for introducing a spinal fixation rod to position the rod to extend along the patient's spinal column. In particular, tool 1100 can be used to engage a rod and introduce the rod through a cannula or an access port, directly through an incision, or through other devices known in the art. As shown, the tool 1100 generally includes an elongate shaft 1112 having proximal and distal ends 1112p, 1112d with an inner lumen 1112c extending therebetween. A pusher shaft (not shown) extends through the elongate shaft 1112 and it preferably includes a proximal end that is coupled to a trigger 1118, and a distal end that is coupled to a pivoting element 1114. The trigger 1118 functions to move the pusher shaft and thereby rotate a rod 1170 coupled to the pivoting element 1114 between a first orientation, in which the rod 1170 is substantially coaxial with the longitudinal axis L' of the shaft 1112, as shown in FIG. 11A, and a second orientation, in which the rod 1170 extends in a direction transverse to the elongate shaft 1112, as shown in FIG. 11B. The tool 1100 can also include a mechanism for removably engaging the rod 1170 to allow the rod 1170 to be subsequently released from the tool 1100 after it is disposed in the patient's body.

In use, the rod 1170 is engaged by the tool and it is introduced through an access port or an incision in the first orientation shown in FIG. 11A. The trigger 1118 can then be engaged to rotate or pivot the rod 1170 into the second orientation, as shown in FIG. 11B, thereby positioning the rod substantially parallel to the patient's spinal column. The rod 1170 can then be released from the tool 1100 and attached to the rod-engaging member 414 of the guide system 100, 410, 900. In an alternative embodiment, the tool 1100, or a variation of the tool 1100, can be formed integrally with the guide system 100, 410, 900 such that the tool 1100 functions as the rod-engaging member.

The tool 1100, and other embodiments of tools for introducing a rod, are described in more detail in U.S. patent application Ser. No. 10/737,538 of Techiera et al. filed on Dec. 16, 2003 and entitled "Pivoting Implant Holder," which is incorporated by reference herein in its entirety. This patent application also discloses techniques for engaging a spinal fixation element, and such techniques can optionally be incorporated into system 100, 410, 900 to couple a rod to the rod-engaging member 414.

Regardless of the technique used to insert the rod within the patient's body, the rod may be attached to the guide system 100, 410, 900 which is maintained in a fixed position, e.g., by attaching the guide system to a support, such as the operating table. The rod can thereafter optionally be used to facilitate targeting of the implant sites.

Position Fixation

Once the rod has been inserted and properly positioned as set forth in FIGS. 9A-E, the position of the rod can be fixed using a anchor system in conjunction with the anchor fixation head of the rod. The interaction of the anchor fixation head and the anchor system has been discussed above in regard to FIG. 2. In many instances the anchor system may be inserted through the incision used to insert the rod. Indeed, tools for used for the insertion of the rod, such as the cannula 1012 of FIG. 10A can be used to insert the anchor system.

In embodiments where the rod engaging portion of the guide system is a cannula, the cannula may be used to insert the anchor system. An example of this can be seen in FIG. 12.

Figure 12:
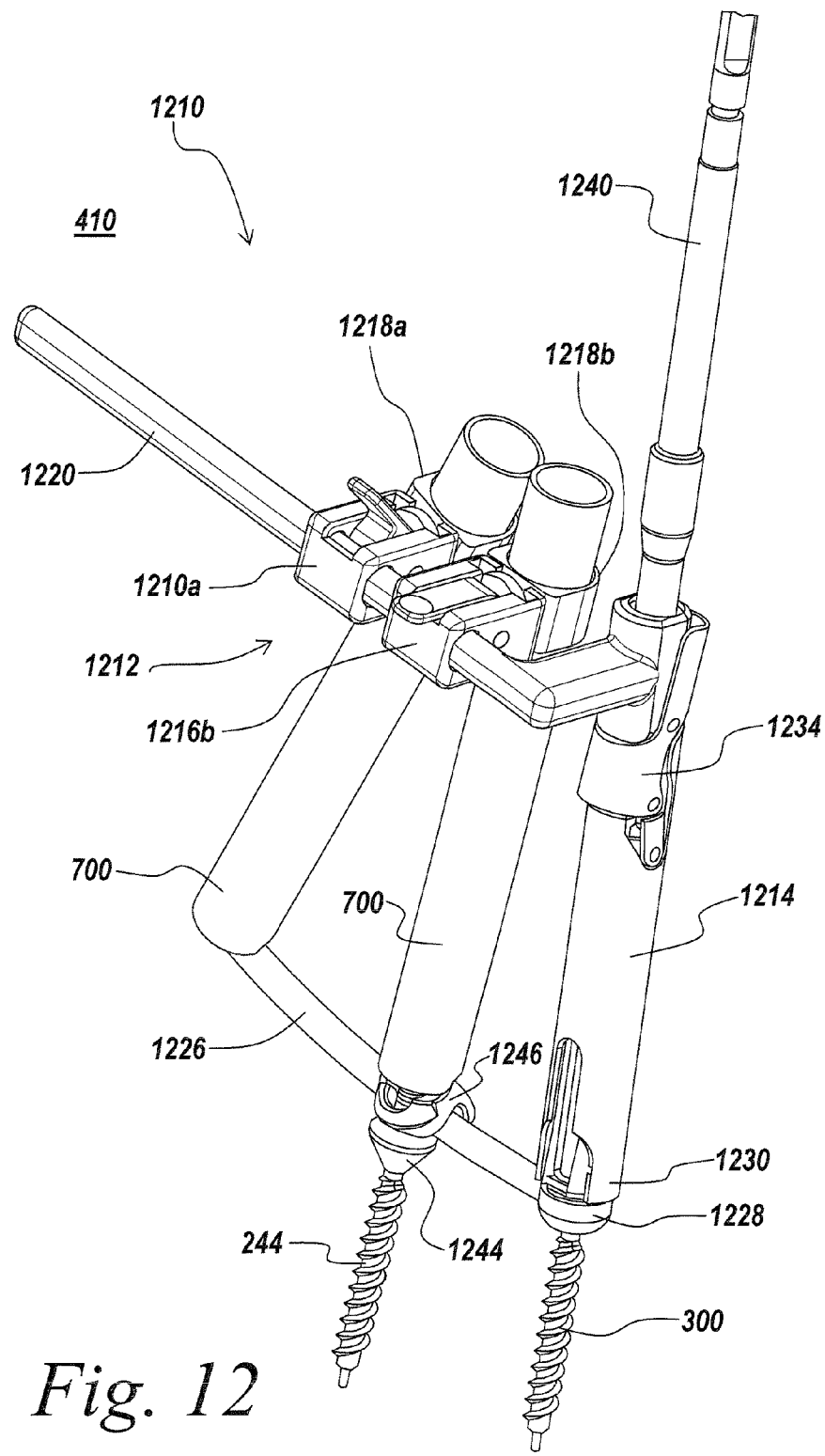
FIG. 12 illustrates an example of a guide system of the present invention being used to insert rod anchoring systems of the present invention.

FIG. 12 illustrates a guide system 1210, similar to that the one illustrated in FIGS. 1 and 4, which is coupled to a rod 1226 and used to insert rod anchoring systems 300, 244. As shown, the guide system 1210 generally includes a guide portion 1212 that is adapted to be positioned outside a patient's body and a rod-engaging portion 1214 that is a cannula adapted to couple to a rod 1226, to maintain the rod 1226 in a fixed position within the patient's body such that the rod 1226 extends adjacent to a patient's spinal column. The rod-engaging portion 1214 may be effective to maintain the rod 1226 in a position that is substantially parallel to, but spaced apart from, the guide portion 1212 such that guide portion 1212 serves as a guide located outside of the body to indicate the location of the rod 1226 disposed inside the patient's body. The guide system 1210 can also include one or more targeting instruments 1216a, 1216b that are movably coupled to the guide portion 1212 of the system 1210. The targeting instruments 1216a, 1216b can be adapted to target an implant site on a vertebra in the patient's spinal column.

In the example, the rod-engaging portion 1214 of the guide system is coupled to the rod 1226 at the anchor fixation head 1228 and locked in place using a locking mechanism 1230 which mates with surface configurations on the rod fixation head as shown in FIG. 2. Once the guide system 1210 is locked into place, the cannula of the rod engaging portion 1214 can be used to insert a anchor system 300 into the anchor fixation head 1228. In this embodiment, the anchor system inserted is the anchor screw system of FIG. 3.

As previously discussed above the anchor screw system includes two parts: an anchor screw 310 and a set screw 320. In use, the anchor screw is inserted first using insertion tool 1240 to engage the anchor fixation head 1228 of the rod 1226. The head portion 314 of the anchor screw is configured to mate anchor fixation head 1228 to fix the location of the rod but still allow pivoting of the rod 1226 on the head portion 314. Once the desired orientation for the rod 1226 is obtained, the set screw 320 can be inserted using insertion tool 1240 to fix the position of the rod 1226. In certain embodiments, the set screw 320 has channel 324 that allows further adjustment of the anchor screw 310 after the set screw has been inserted.

In another embodiment, a anchor bolt system may be used to fix the position of the rod 1226. The anchor bolt system includes an anchor bolt and a nut. In certain embodiments, where an anchor bolt system is used, the anchor bolt may be place before the rod 1226. The rod 1226 is then inserted so that anchor fixation head 1228 of the rod 1226 engages the anchor bolt. An example of an anchor bolt 244 and its interaction with a corresponding anchor fixation head 242 was described in above in regard to FIG. 2. Once the anchor fixation head has engaged the anchor bolt 244, a nut (not shown) can be inserted to secure the anchor fixation head 242 to the anchor bolt 244.

It should be understood that the above discussed embodiments are but a few of the possible method for fixing the position of the rod. Other possible techniques and embodiments will be apparent to one skilled in the art given the benefit of this disclosure.

Targeting

Once the rod is fixed in position and attached to the guide system 410, 1210 the targeting instruments can be used to identify a target implant site on one or more vertebrae. In particular, an imaging device 600 can be placed over the targeting members 418a, 418b, 1218a, 1218b to align the targeting members 418a, 418b, 1218a, 1218b with the target implant sites on the underlying vertebra. Once aligned, the targeting members 418a, 418b, 1218a, 1218b may be locked in place relative to the support 420, 1220 on the guide system 410, 1210. The surgeon can then mark the incision location on the skin below the targeting members 418a, 418b, 1218a, 1218b. Alternatively, a further incision is not needed, and targeting and pedicle screw insertion can be effected through the incision through which the rod is placed. As previously noted, exemplary methods and devices for targeting an implant site are described in more detail in U.S. Publication No. 2003/0187431 of Simonson entitled "Apparatus and Method for Targeting for Surgical Procedures," which is incorporated by reference herein in its entirety.

Once the implant sites on the vertebrae are targeted, the targeting members 418a, 418b, 1218a, 1218b can remain attached to the guide system 410, 1210 to allow tools and devices, such as cannulae 700, to be inserted or attached.

Implanting Additional Anchors

Once the target implant sites are identified, additional anchor systems can be implanted at one or more implant sites. Any type of conventional anchor system can be used to couple a rod, statically or dynamically, to one or more vertebrae. For illustration purposes, however, exemplary methods will be described in connection with anchor systems for use with rod first techniques. An example of such a anchor system is an anchor bolt system.

In one exemplary embodiment, the anchor bolt can be adapted to receive the rod from the side such that the rod is adjacent to the bolt. An example of such a bolt can be seen in FIGS. 2 and 11. In the example of FIG. 12, the anchor bolt 244 has a seat 1244 for receiving the rod 1226. Once the rod 1226 is seated on the seat 1244, a capturing mechanism 1246, may placed and secured with a nut (not shown) to connect the rod 1226 to the anchor bolt 244. Further examples and discussion of anchor systems can be found in related applications DUQ-032 entitled "Offset Connection Bone Anchor Assembly," filed on Aug. 31, 2007; DUQ-033 entitled "Adaptable Clamping Mechanism for Coupling a Spinal Fixation Element to a Bone Anchor," filed on Aug. 31, 2007; DUQ-036 entitled "Spanning Connector For Connecting A Spinal Fixation Element And An Offset Bone Anchor," filed on Aug. 31, 2007; and DUQ-37 entitled "Method and System for Securing a Rod to a Bone Anchor with a Connector," filed on Aug. 31, 2007.

Figure 13A:
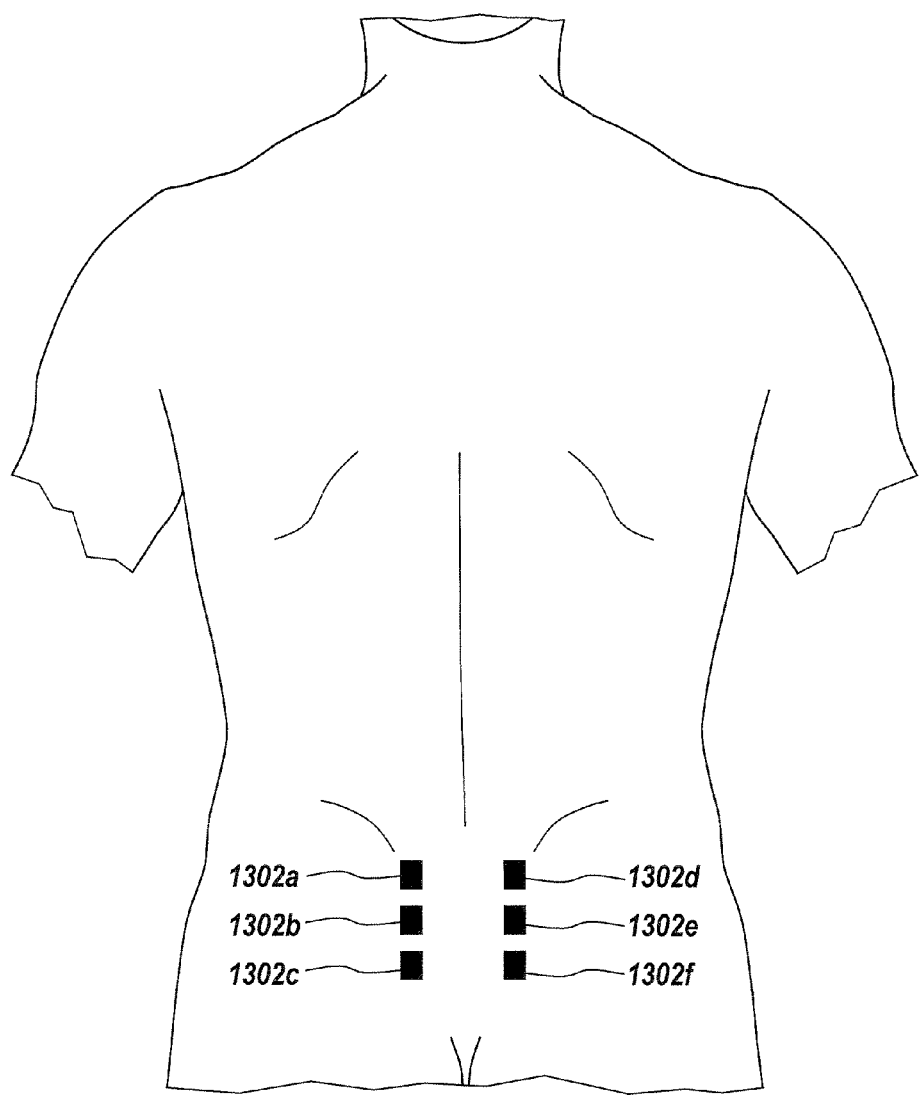
FIG. 13A is a posterior view of six percutaneous incisions formed in the thoracolumbar fascia of a patient's back.

Various techniques can be used to implant the anchors systems; for example a minimally invasive percutaneous incision 1302 may be made through the tissue at one or more of the sites. The location, shape, and size of the incision 1302 will depend on the type and quantity of anchor systems being implanted, as well as the technique being employed to implant the anchor systems. By way of non-limiting example, FIG. 13A illustrates three minimally invasive percutaneous incisions 1302a-c formed on one side of three adjacent vertebra in the thoracolumbar fascia in the patient's back, and three additional minimally invasive percutaneous incisions 1302d-f formed on the opposite side of the three adjacent vertebra in the thoracolumbar fascia in the patient's back. While not shown, a guide system 410, 1210 can be positioned adjacent to each set of incisions 1302a-c, 1302d-f with a targeting member in alignment with each incision.

Figure 13B:
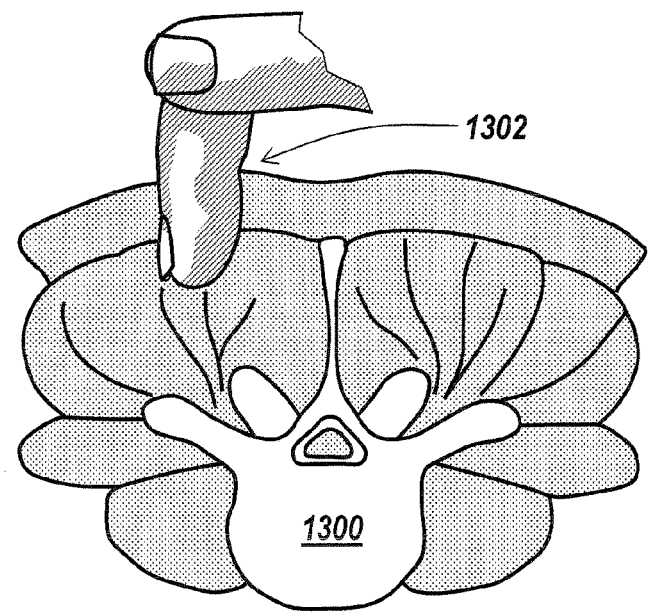
FIG. 13B is an end view showing a blunt dissection of the muscles surrounding a patient's vertebra.

In certain exemplary embodiments, one or more of the incisions may be expanded to create a pathway from the incision 1302 to proximate a vertebra 1300. For example, the incision 1302 may be expanded by serial dilation, with a retractor such as an expandable retractor, or by any other conventional techniques. In one exemplary embodiment, blunt finger dissection can be used, as shown in FIG. 13B, to separate the longissimus thoracis and multifidus muscles, thereby exposing the facet and the junction of the transverse process and superior articular process.

Figure 13C:
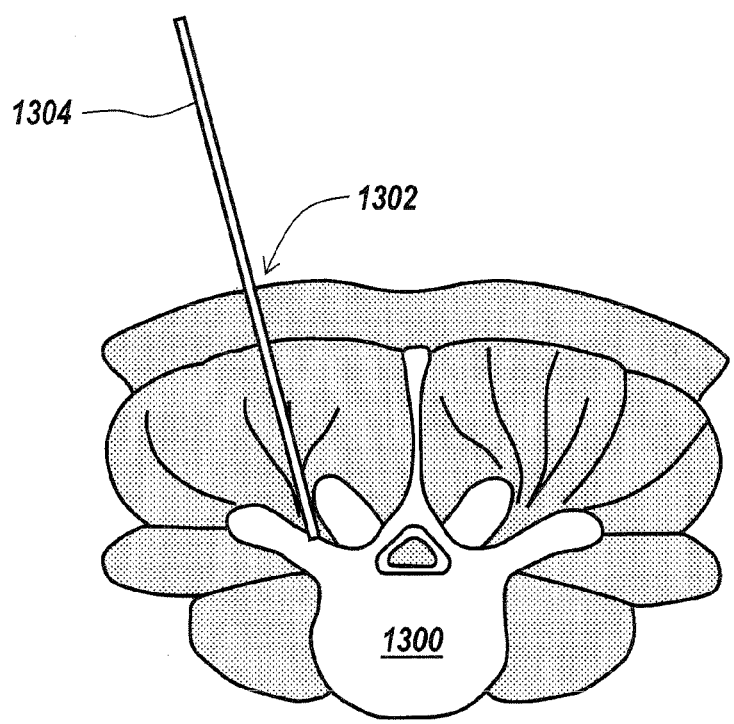
FIG. 13C is an end view of the vertebra in FIG. 13B with a k-wire placed through the incision and into the patient's vertebra.
Figure 13D:
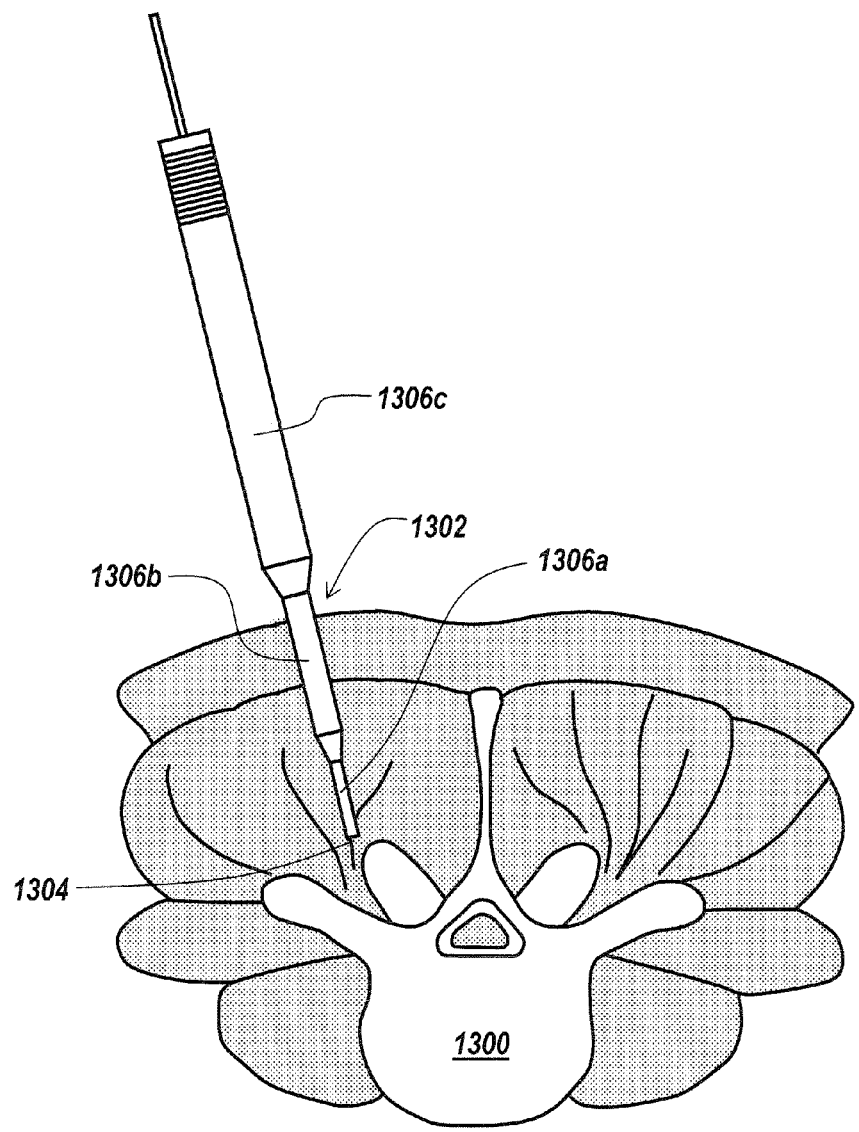
FIG. 13D is an end view of the vertebra in FIG. 13C showing an obturator and several dilators disposed over the k-wire to dilate the tissue and muscles.

An anchor system may be inserted through one or more of the incisions and the pathways to proximate the vertebra 1300. Any technique for implanting an anchor system can be used. In one embodiment, for example, an anchor system can be implanted over a guidewire, such as a k-wire. As shown in FIG. 13C, a guide wire, e.g., a k-wire 1304, can be implanted, either prior to or after formation of the incision 1302, at each anchor implant site. The k-wire 1304 may extend into the vertebra 1300 at the desired entry point of the anchor system. In certain exemplary embodiments, the k-wire may be advanced into the vertebra 1300. In other exemplary embodiments, the k-wire may be positioned proximate to or against the vertebra 1300. Fluoroscopy or other imaging may be used to facilitate proper placement of the k-wire 1304. The incision 1302 may be dilated to provide a pathway for delivery of a anchor system to each implant site, in the manner discussed above, before or after placement of the guidewire. For example, FIG. 13D illustrates serial dilation at one end of the incision 1302 using an obturator 1306a having several dilators 1306b, 1306c of increasing size placed there over. The dilators 1306b, 1306c are delivered over the obturator 1306a and k-wire 1304 to essentially stretch the skin around the incision 1302 and to expand the pathway to the anchor site. While not shown, the obturator 1306a and the dilators 1306b, 1306c can extend through the targeting members 418a, 418b, 1218a, 1218b on the guide system 410, 1210, or alternatively the targeting members 418a, 418b, 1218a, 1218b can be removed from the guide system 410, 1210 and the obturator 1306a and dilators 1306b, 1306c can merely be guided along the k-wire.

One skilled in the art will appreciate that a anchor system may be advanced to a vertebra through the incision without the need for a guidewire.

Once the incision 1302 is dilated to the proper size, if necessary, the vertebra 1300 may be prepared using one or more bone preparation instruments, such as drills, taps, awls, burrs, probes, etc. In certain exemplary embodiments, one or more cannulae can be used to provide a pathway from the incision 1302 to the anchor site for insertion of the bone preparation instruments and/or the anchor. In an exemplary embodiment, a relatively small cannula 700 (not shown) may be used to introduce bone preparation instruments into the surgical site. The cannula 700 may be placed through a targeting member 418a, 418b, 1218a, 1218b on the guide system 410, 1210, such that the cannula 700 is in alignment with the target implant site. Once the vertebra 1300 is prepared, a anchor system can be delivered along the k-wire, either through the cannula 700, or after the cannula 700 is removed, and implanted in the vertebra 1300. Alternatively, in embodiments not employing a guidewire, the anchor system may be advanced through the incision, e.g., through a cannula 700, to the vertebra 1300. A cannula, retractor, or other instrument may be employed to guide the anchor system to the vertebra 1300.

This procedure, and other minimally invasive methods and devices for implanting a anchor system, are described in more detail in U.S. patent application Ser. No. 11/163,963 of Ludwig et al. filed on Nov. 4, 2005, entitled "Minimally Invasive Spinal Fixation System and Methods," U.S. patent application Ser. No. 10/738,130 of Anderson et al. entitled "Methods And Devices For Minimally Invasive Spinal Fixation Element Placement," U.S. patent application Ser. No. 10/737,537 of Anderson et al. entitled "Methods And Devices For Spinal Fixation Element Placement," and U.S. patent application Ser. No. 10/738,286 filed on Dec. 16, 2003 and entitled "percutaneous access device and bone anchor assembly." These references are incorporated by reference herein in their entirety.

A person having ordinary skill in the art will appreciate that the aforementioned methods and devices for implanting anchor systems can be modified depending on the type of anchor being implanted, as well as the specific procedure being employed. Moreover, other methods and devices known in the art can be used in accordance with the present invention.

A person skilled in the art will appreciate that a variety of other techniques can be used to couple a rod to the anchor systems. Moreover, the rod does not need to be directly attached to each anchor, and it can be indirectly attached to the anchors using, for example, a band clamp, or slotted or offset connectors. Once the rod is fully seated in the receiver head of each anchor system, a closure mechanism can be applied to each receiver head to retain the rod therein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. A minimally invasive rod-first spinal fixation system, the system comprising:
   a spinal fixation rod having an anchor fixation head;
   an anchor system attached to the anchor fixation head of the spinal fixation rod to anchor the spinal fixation rod to a spinal column; and
   a guide system attached to the anchor fixation head of the spinal fixation rod to insert one or more additional anchor systems, the guide system comprising:
      a guide portion extending along the spinal fixation rod, wherein the guide indicates a location of the spinal fixation rod in a patient;
      one or more targeting members, each adapted to target an implant site on a vertebra of the spinal column, each targeting member being slidably coupled to the guide portion and configured to slide along the guide portion parallel to the spinal fixation rod so that a position of the targeting member is adjusted relative to the target implant site, and the targeting members each having an inner lumen sized and shaped to receive a cannula; and
      a support for coupling a selected targeting member to the guide portion, wherein the selected targeting member is adjustable angularly relative to the support and the selected targeting member may be moved laterally towards or away from the support; and
      a locking mechanism locking the position of the support on the guide portion, wherein the locking mechanism comprises a cam mechanism.

2. The system of claim 1, wherein the anchor fixation head has configurations for attaching the guide system to the rod.

3. The system of claim 1, wherein the anchor system for anchoring the rod using the anchor fixation head comprises an anchor screw system.

4. The system of claim 3, wherein the anchor fixation head of the rod comprises an eyelet configured to receive the anchor screw system.

5. The system of claim 1, wherein the anchor system comprises an anchor bolt system.

6. The system of claim 1, wherein the guide system comprises:
a rod-engaging member mated to the guide portion and adapted to couple to the anchor fixation head of the rod to maintain the rod in a fixed position within a patient's body such that the rod extends adjacent to the spinal column, wherein the guide portion is adapted to be positioned outside the patient's body.

7. The system of claim 6, wherein the rod-engaging member is effective to maintain the rod in a fixed position that is spaced a distance apart from the guide portion and substantially parallel to the guide portion.

8. The system of claim 7, wherein the guide portion is offset from the fixed position of the rod allowing for the plurality of targeting members to target an implant site on a vertebra inline with the rod.

9. The system of claim 6, wherein the rod engaging member comprises a cannula for inserting the anchor system into the anchor fixation head of the rod.

* * * * *